US 9,770,160 B2

(12) United States Patent
Okaniwa et al.

(10) Patent No.: US 9,770,160 B2
(45) Date of Patent: Sep. 26, 2017

(54) BENDING TUBE FOR ENDOSCOPE, ENDOSCOPE AND METHOD FOR MANUFACTURING BENDING TUBE FOR ENDOSCOPE

(71) Applicant: OLYMPUS CORPORATION, Tokyo (JP)

(72) Inventors: Suguru Okaniwa, Hachioji (JP); Takanori Watanabe, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/173,841

(22) Filed: Jun. 6, 2016

(65) Prior Publication Data
US 2016/0278617 A1   Sep. 29, 2016

Related U.S. Application Data

(63) Continuation of application No. PCT/JP2015/057464, filed on Mar. 13, 2015.

(30) Foreign Application Priority Data

Apr. 15, 2014   (JP) ................................ 2014-083858

(51) Int. Cl.
*A61B 1/00* (2006.01)
*A61B 1/008* (2006.01)
(Continued)

(52) U.S. Cl.
CPC ........ *A61B 1/0052* (2013.01); *A61B 1/00009* (2013.01); *A61B 1/0011* (2013.01); (Continued)

(58) Field of Classification Search
CPC . A61B 1/0052; A61B 1/00009; A61B 1/0011; A61B 1/00121; A61B 1/0055; (Continued)

(56) References Cited

U.S. PATENT DOCUMENTS 3,799,151 A * 3/1974 Fukaumi ............. A61B 1/0055
600/142
5,179,935 A * 1/1993 Miyagi ................ A61B 1/0055
600/108

(Continued)

FOREIGN PATENT DOCUMENTS

JP    S62-114525 A    5/1987
JP    H03-063025 A    3/1991
(Continued)

OTHER PUBLICATIONS

International Search Report dated Jun. 9, 2015 issued in PCT/JP2015/057464.

(Continued)

*Primary Examiner* — John P Leubecker
*Assistant Examiner* — Rajaa El Alami
(74) *Attorney, Agent, or Firm* — Scully, Scott, Murphy & Presser, P.C.

(57) ABSTRACT

A bending tube for an endoscope, which is provided inside a bending portion of an insertion portion of an endoscope and includes a plurality of bending pieces covered by a flexible tube body, the bending tube including a distalmost end bending piece connected to a distal end portion of an insertion portion, a proximalmost end bending piece connected to a flexible tube portion of the insertion portion, and a net-like tube covering an outer periphery of the plurality of bending pieces except the distalmost end bending piece and the proximalmost end bending piece and including a distal end part fixed to a first bending piece joined to the distalmost end bending piece and a proximal end part fixed to a second bending piece joined to the proximalmost end bending piece.

10 Claims, 6 Drawing Sheets

(51) Int. Cl.
    *A61B 1/005*     (2006.01)
    *A61B 1/05*     (2006.01)
    *A61B 1/06*     (2006.01)
    *G02B 23/24*     (2006.01)

(52) U.S. Cl.
    CPC ........ *A61B 1/0055* (2013.01); *A61B 1/00121* (2013.01); *A61B 1/051* (2013.01); *A61B 1/06* (2013.01); *G02B 23/2476* (2013.01)

(58) Field of Classification Search
    CPC ......... A61B 1/05; A61B 1/06; A61B 1/00142; A61B 1/00135; A61B 1/00078; A61B 1/00075
    See application file for complete search history.

(56) References Cited

U.S. PATENT DOCUMENTS

| | | | | |
|---|---|---|---|---|
| 8,206,287 | B2* | 6/2012 | Matsuo | A61B 1/0055 600/140 |
| 8,226,547 | B2* | 7/2012 | Tsutsumi | A61B 1/0008 600/127 |
| 8,591,404 | B2* | 11/2013 | Yamazaki | A61B 1/0057 600/139 |
| 8,905,919 | B2* | 12/2014 | Matsuo | A61B 1/0056 600/139 |
| 9,462,932 | B2* | 10/2016 | Ostrovsky | A61B 1/0055 |
| 2005/0272975 | A1* | 12/2005 | McWeeney | A61B 1/00071 600/113 |
| 2005/0288656 | A1* | 12/2005 | Koerner | A61B 18/02 606/21 |
| 2006/0111617 | A1* | 5/2006 | Wimmer | A61B 1/00078 600/146 |
| 2007/0233040 | A1* | 10/2007 | Macnamara | A61B 1/00071 604/523 |
| 2009/0012358 | A1* | 1/2009 | Ichihashi | A61B 1/00105 600/110 |
| 2010/0076266 | A1* | 3/2010 | Boulais | A61B 1/00059 600/142 |
| 2010/0168519 | A1* | 7/2010 | Matsuo | A61B 1/00071 600/139 |
| 2013/0035549 | A1* | 2/2013 | Abe | A61B 1/0011 600/121 |
| 2013/0041224 | A1* | 2/2013 | Okaniwa | A61B 1/0055 600/142 |
| 2014/0163321 | A1* | 6/2014 | Seto | A61M 25/0138 600/139 |
| 2015/0305598 | A1* | 10/2015 | Yamashita | A61B 1/00078 604/95.04 |
| 2016/0029878 | A1* | 2/2016 | Yamazaki | A61B 1/0057 600/138 |
| 2017/0020366 | A1* | 1/2017 | Watanabe | A61B 1/00 |

FOREIGN PATENT DOCUMENTS

| | | |
|---|---|---|
| JP | H05-023290 A | 2/1993 |
| JP | H09-201328 A | 8/1997 |
| JP | H09-276210 A | 10/1997 |
| JP | 2003-126024 A | 5/2003 |

OTHER PUBLICATIONS

Japanese Office Action dated Nov. 17, 2015 issued in JP 2015-539899.

* cited by examiner

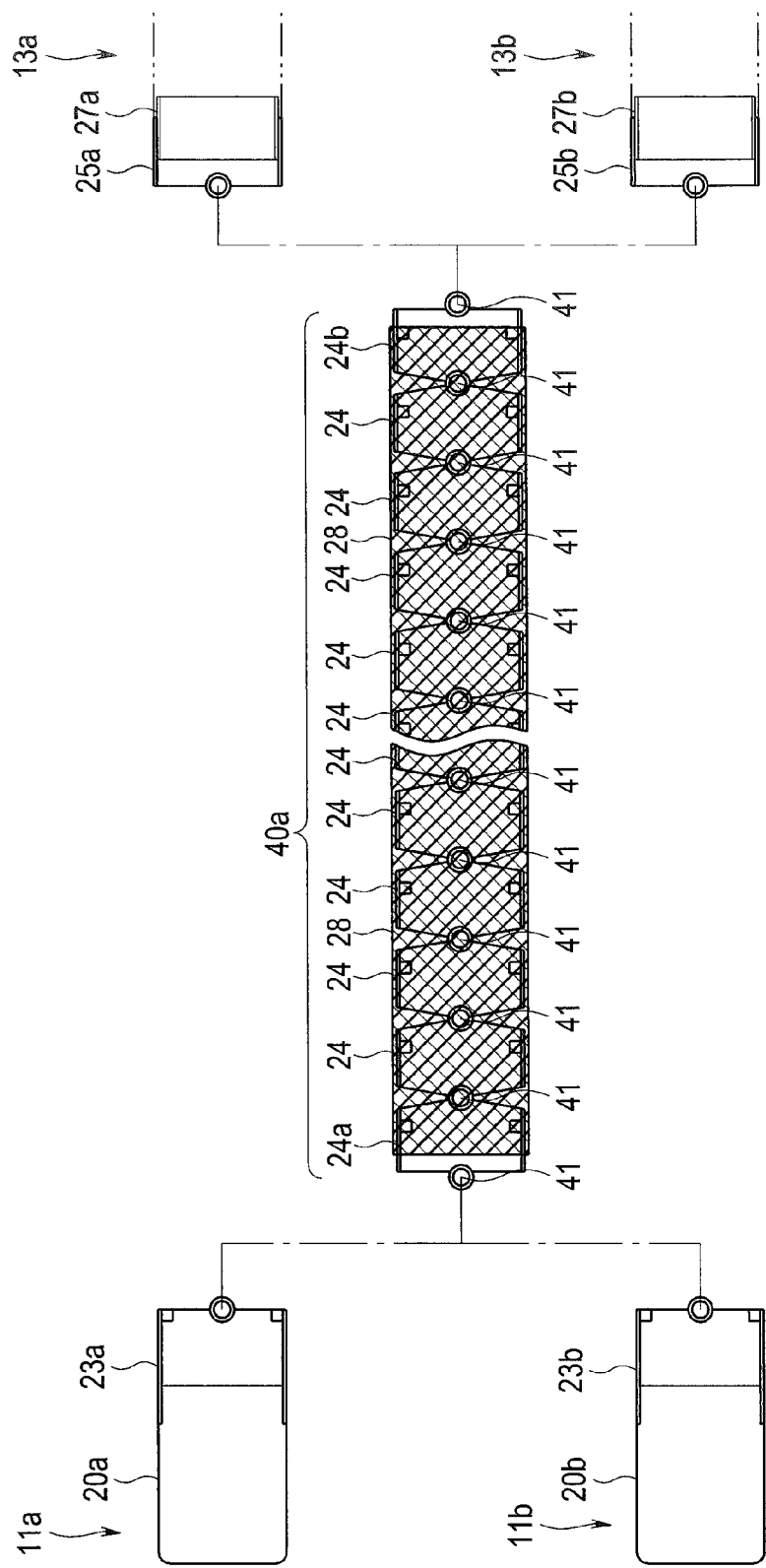

BENDING TUBE FOR ENDOSCOPE, ENDOSCOPE AND METHOD FOR MANUFACTURING BENDING TUBE FOR ENDOSCOPE

CROSS REFERENCE TO RELATED APPLICATION

This application is a continuation application of PCT/JP2015/057464 filed on Mar. 13, 2015 and claims benefit of Japanese Application No. 2014-083858 filed in Japan on Apr. 15, 2014, the entire contents of which are incorporated herein by this reference.

BACKGROUND OF THE INVENTION

1. Field of the Invention

The present invention relates to a bending tube for an endoscope, which is provided in an insertion portion of an endoscope, an endoscope including the bending tube for an endoscope and a method for manufacturing the bending tube for an endoscope.

2. Description of the Related Art

Conventionally, endoscopes including an insertion portion that can be inserted into a subject/object that cannot directly be viewed by an observer are used in order to observe the subject/object. For enhancement in insertability of the insertion portion, some of the endoscopes are provided with a bending portion, which is bent via manual operation.

In recent years, in order to insert the insertion portion into a limited space of a subject/object for, e.g., observation, various ingenuities have been taken to enhance the insertability of the insertion portion, and for example, Japanese Patent Application Laid-Open Publication No. 9-201328 discloses a technique of an endoscope with a reduced diameter of a part that can have a maximum diameter in a bending portion and reduced irregularities in an outer surface of the bending portion.

SUMMARY OF THE INVENTION

A bending tube for an endoscope according to an aspect of the present invention is a bending tube for an endoscope, the bending tube being provided inside a bending portion of an insertion portion of an endoscope and including a plurality of bending pieces pivotally joined to one another and covered by a soft outer covering, the bending tube including: among the plurality of bending pieces, a distalmost end bending piece connected to a distal end portion of the insertion portion; among the plurality of bending pieces, a proximalmost end bending piece connected to a flexible tube portion of the insertion portion; a first bending piece including a distal end part pivotally joined to the distalmost end bending piece, the first bending piece having an outer diameter smaller than an outer diameter of the distalmost end bending piece; a second bending piece including a proximal end part pivotally joined to the proximalmost end bending piece, the second bending piece having an outer diameter smaller than an outer diameter of the proximalmost end bending piece; and a net-like tube covering the plurality of bending pieces except the distalmost end bending piece and the proximalmost end bending piece, the net-like tube including a distal end part and a proximal end part fixed to an outer peripheral face of the first bending piece and an outer peripheral face of the second bending piece, respectively.

An endoscope according to an aspect of the present invention is an endoscope including a bending tube for an endoscope, the bending tube being provided inside a bending portion of an insertion portion and including a plurality of bending pieces pivotally joined to one another and covered by a soft outer covering, the bending tube including: among the plurality of bending pieces, a distalmost end bending piece connected to a distal end portion of the insertion portion; among the plurality of bending pieces, a proximalmost end bending piece connected to a flexible tube portion of the insertion portion; a first bending piece including a distal end part pivotally joined to the distalmost end bending piece, the first bending piece having an outer diameter smaller than an outer diameter of the distalmost end bending piece; a second bending piece including a proximal end part pivotally joined to the proximalmost end bending piece, the second bending piece having an outer diameter smaller than an outer diameter of the proximalmost end bending piece; and a net-like tube covering the plurality of bending pieces except the distalmost end bending piece and the proximalmost end bending piece, the net-like tube including a distal end part and a proximal end part fixed to an outer peripheral face of the first bending piece and an outer peripheral face of the second bending piece, respectively.

A method for manufacturing a bending tube for an endoscope according to an aspect of the present invention is a method for manufacturing a bending tube for an endoscope, the bending tube being provided inside a bending portion of an insertion portion in an endoscope and including a plurality of bending pieces pivotally joined and covered by a soft outer covering, the method including: pivotally joining a plurality of small-diameter bending pieces except a distalmost end bending piece connected to a distal end portion of the insertion portion and a proximalmost end bending piece connected to a flexible tube portion of the insertion portion from among the plurality of bending pieces, the plurality of small-diameter bending pieces having an outer diameter smaller than an outer diameter of the distalmost end bending piece and an outer diameter of the proximalmost end bending piece; covering an outer periphery of the plurality of small-diameter bending pieces joined, by a net-like tube; and fixing opposite ends of the net-like tube to opposite ends of the plurality of small-diameter bending pieces joined, respectively.

BRIEF DESCRIPTION OF THE DRAWINGS

FIG. 7 relates to an aspect of the present invention and indicates a modification, and is a schematic diagram illustrating a configuration of a bending tube unit to be used in common for distal end portions and flexible tube portions having different specifications.

DETAILED DESCRIPTION OF THE PREFERRED EMBODIMENTS

Figure 1:
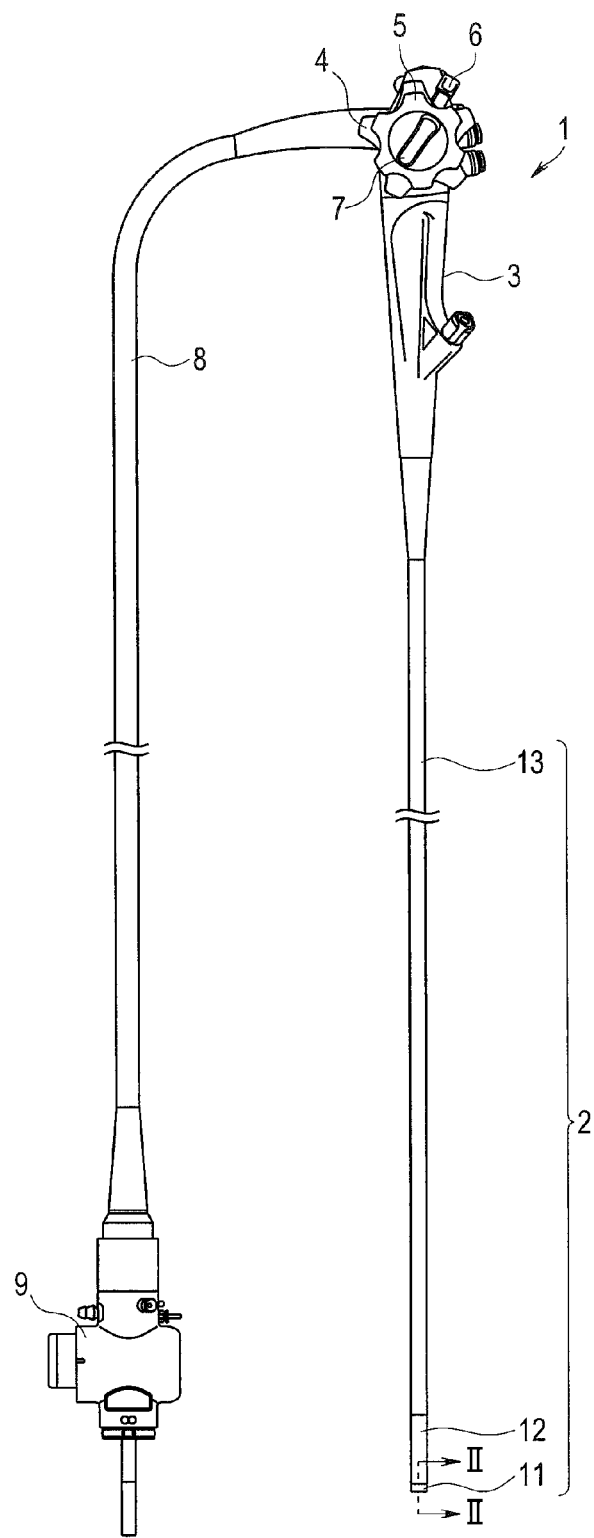
FIG. 1 relates to an aspect of the present invention and is a diagram illustrating an overall configuration of an endoscope.

The present invention will be described below with reference to the drawings. Note that in each of the drawings used for the below description, components are illustrated on difference scales so that the respective components have sizes that are large enough to be recognized in the drawing, and the present invention is not limited only to the counts and amounts, and the shapes of the components, and the size ratios and the relative positional relationships among each of the components illustrated in the drawings.

Figure 2:
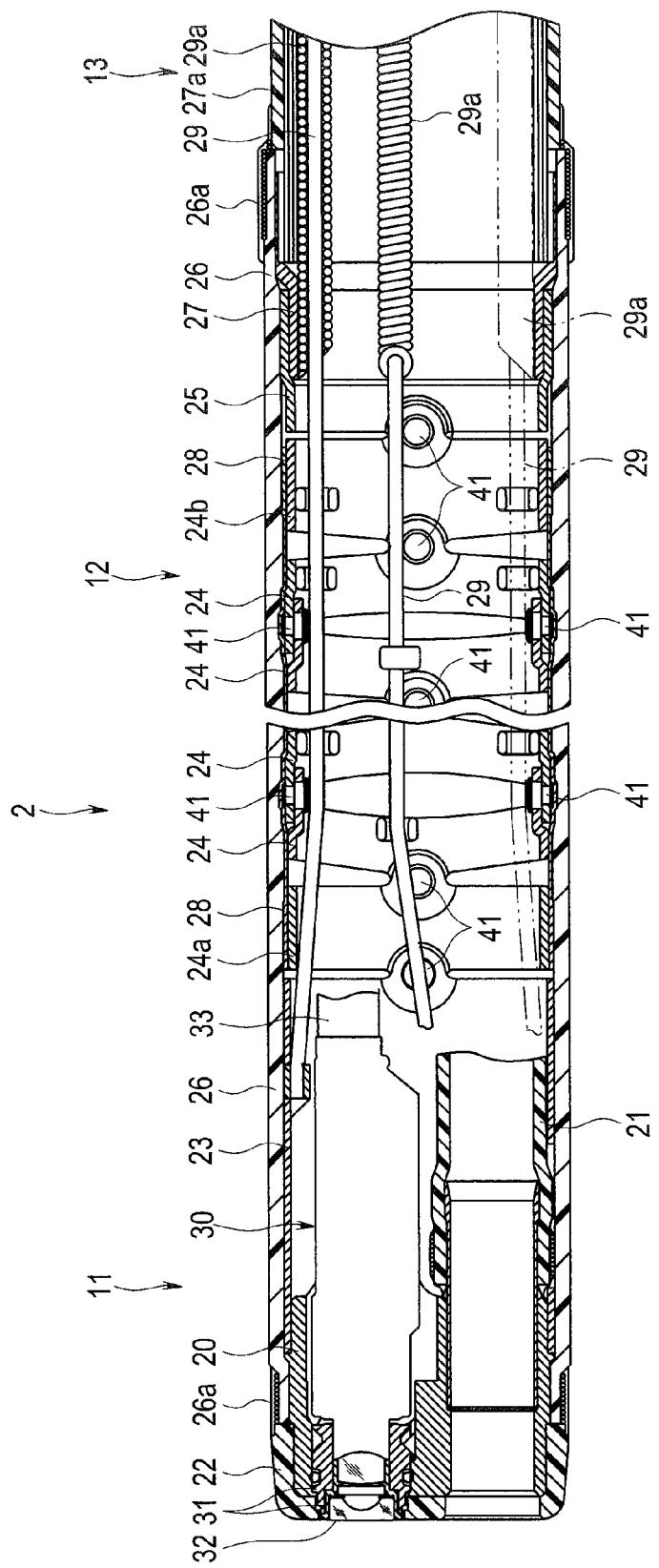
FIG. 2 relates to an aspect of the present invention and is a cross-sectional diagram illustrating a configuration of a distal end part of an insertion portion along line II-II in FIG. 1.
Figure 3:
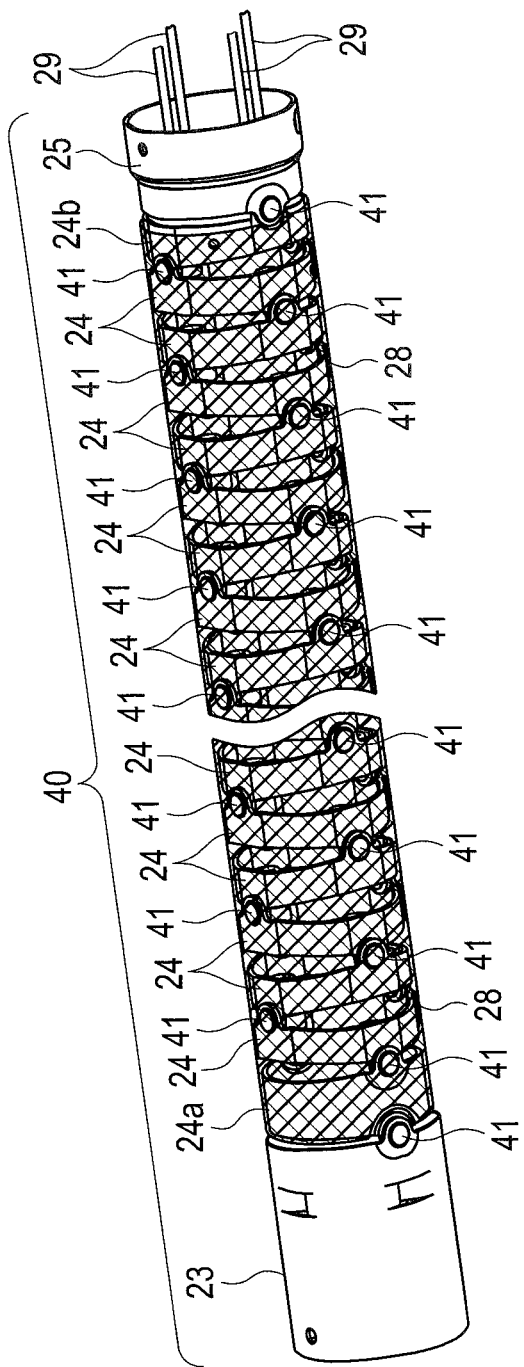
FIG. 3 relates to an aspect of the present invention and is a perspective diagram illustrating a configuration of a bending tube covered by a braid.
Figure 4:
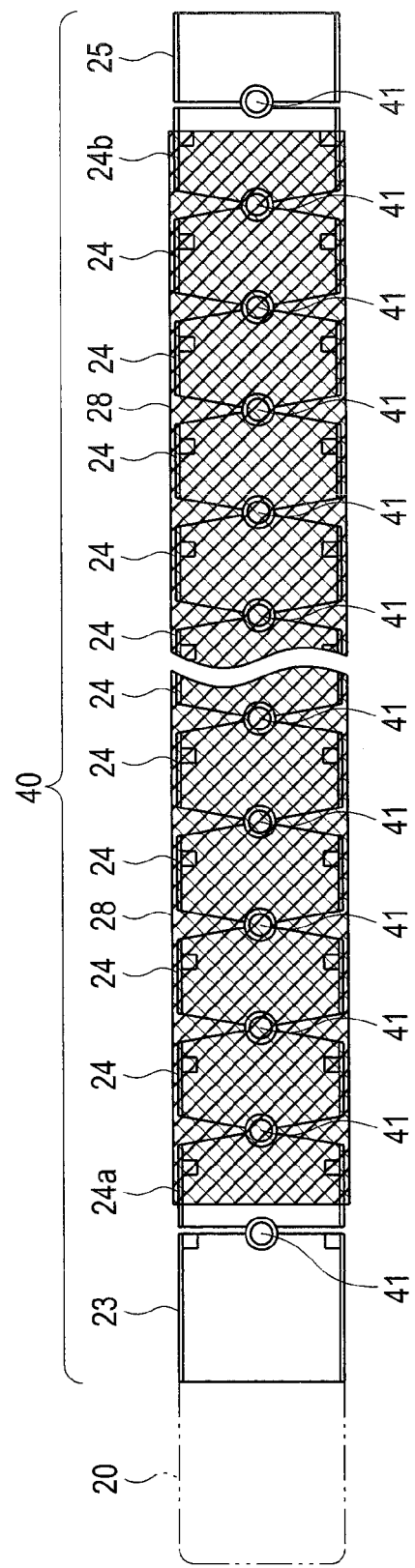
FIG. 4 relates to an aspect of the present invention and is a schematic diagram illustrating the configuration of the bending tube covered by the braid, with operation wires not illustrated.
Figure 5:
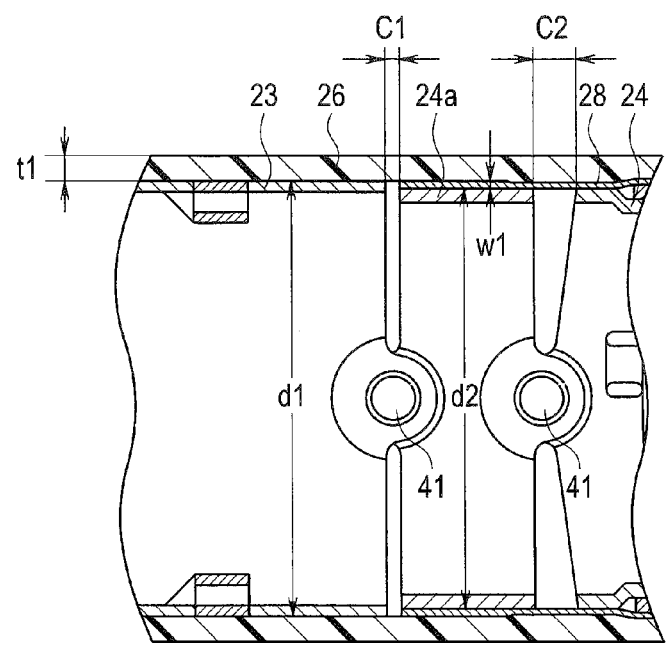
FIG. 5 relates to an aspect of the present invention and is a cross-sectional diagram illustrating a configuration of the distal end side of the bending tube.
Figure 6:
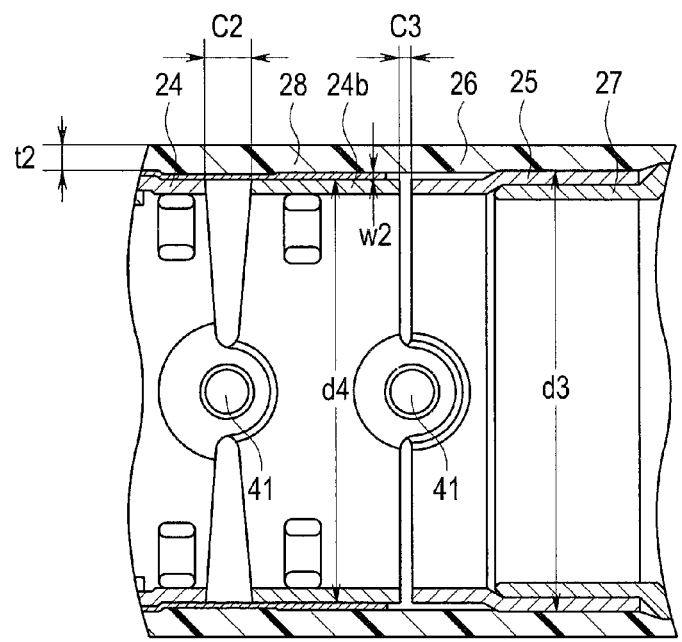
FIG. 6 relates to an aspect of the present invention and is a cross-sectional diagram illustrating a configuration of the proximal end side of the bending tube.

FIGS. 1 to 7 relate to an aspect of the present invention: FIG. 1 is a diagram illustrating an overall configuration of an endoscope; FIG. 2 is a cross-sectional diagram illustrating a configuration of a distal end part of an insertion portion along line II-II in FIG. 1; FIG. 3 is a perspective diagram illustrating a configuration of a bending tube covered by a braid; FIG. 4 is a schematic diagram illustrating the configuration of the bending tube covered by the braid, with operation wires not illustrated; FIG. 5 is a cross-sectional diagram illustrating a configuration of the distal end side of the bending tube; FIG. 6 is a cross-sectional diagram illustrating a configuration of the proximal end side of the bending tube; and FIG. 7 indicates a modification and is a schematic diagram illustrating a configuration of a bending tube unit to be used in common for distal end portions and flexible tube portions having different specifications.

As illustrated in FIG. 1, an endoscope 1 includes an insertion portion 2 to be inserted into a subject/object, an operation portion 3 provided so as to be continuous with the proximal end side of the insertion portion 2, a universal cord 8 extending out from the operation portion 3, and a connector 9 provided at an extension end of the universal cord 8. Note that the endoscope 1 is electrically connected to non-illustrated external apparatuses such as a video processor and a light source apparatus via the connector 9.

At the operation portion 3, an upward/downward bending operation knob 4 for bending a bending portion 12 of the insertion portion 2 upward/downward, and a leftward/rightward bending operation knob 5 for bending the bending portion 12 leftward/rightward are provided.

Furthermore, at the operation portion 3, a fixing lever 6 for fixing a pivotal position of the upward/downward bending operation knob 4, and a fixing knob 7 for fixing a pivotal position of the leftward/rightward bending operation knob 5 are provided.

The insertion portion 2 includes a distal end portion 11, the bending portion 12 and a flexible tube portion 13 connected so as to be continuous with one another in this order from the distal end side, and has an elongated shape that enables easy insertion of the insertion portion 2 into a subject/object.

The bending portion 12 is intended to change a direction of observation through a later-described image pickup unit 30 provided inside the distal end portion 11 or enhance insertability of the distal end portion 11 in a subject/object by means of an operation to pivot the upward/downward bending operation knob 4 and the leftward/rightward bending operation knob 5 to bend the bending portion 12 in, for example, four directions: upward, downward, leftward and rightward. Note that detailed description of the bending portion 12 will be provided later.

Inside the distal end portion 11 of the insertion portion 2, as illustrated in FIG. 2, a distal end rigid member 20 is provided, and the image pickup unit 30 that picks up an image of the inside of a subject/object is fixed to the distal end rigid member 20.

Note that in addition to the image pickup unit 30, e.g., a distal end part of a non-illustrated light guide bundle that supplies illuminating light to the inside of a subject/object, the light guide bundle being inserted inside the connector 9, the universal cord 8, the operation portion 3 and the insertion portion 2 illustrated in FIG. 1, and a distal end part of a treatment instrument insertion channel 21 for inserting/removing a treatment instrument to/from the inside of the subject/object are fixed to the distal end rigid member 20 via known fixing means. Also, a distal end cover 22 is disposed on a distal end face of the distal end rigid member 20.

Furthermore, in the distal end rigid member 20, a distal end part of a non-illustrated fluid supply conduit that supplies a fluid to an objective lens 32 exposed at a distal end face of the distal end portion 11, which is an observation window provided in a distalmost end of the image pickup unit 30, is provided, and a non-illustrated supply nozzle or the like is fixed to the distal end part of the fluid supply conduit via known fixing means.

A distalmost end bending piece 23 of the later-described bending portion 12 is fitted on the distal end rigid member 20, and a bending rubber 26, which is a flexible tube body that serves as a soft outer covering, is disposed so as to cover an outer peripheral portion of a plurality of bending pieces 24 (24a, 24b) pivotally provided so as to be continuous with one another and a proximalmost end bending piece 25 and an outer peripheral portion of the distal end rigid member 20.

A distal end part of the bending rubber 26 is fixedly bonded to an outer peripheral part of the distal end rigid member 20 via a yarn wrapping bonding portion 26a. Also, a proximal end part of the bending rubber 26 is fixed to an outer periphery of a connection pipe sleeve 27 provided inside a distal end of the flexible tube portion 13, together with an outer covering 27a covering an outer periphery of the flexible tube portion 13, via a yarn wrapping bonding portion 26a. Also, the bending piece 25 at a proximalmost end of the bending portion 12 is fitted on and fixed to the connection pipe sleeve 27 in the flexible tube portion 13.

The image pickup unit 30 provided inside the distal end portion 11 includes a plurality of lens frames 31, and inside the lens frames 31, as optical members forming an image pickup optical system (optical system), the objective lens 32, which is the aforementioned observation window, a diaphragm provided on a back face of the objective lens 32 and a group of other objective lenses are held.

On the proximal end side of the plurality of lens frames 31, e.g., an image pickup frame, which is not illustrated here, is provided. Note that an image sensor including, e.g., a solid-state image pickup device, which is a CCD or a CMOS, is held inside the image pickup frame. Then, on the proximal end side of the image sensor, e.g., an electric substrate on which a plurality of electronic components are mounted is disposed.

A cable 33 for performing, e.g., supply of various drive signals to the image sensor and transmission of image signals obtained by the image sensor is connected to the image pickup unit 30.

In the image pickup unit 30, a heat-shrinkable tube is provided from a distal end part of the cable 33, and inside the heat-shrinkable tube, a filler such as an adhesive is disposed for keeping water tightness.

Note that other components of the endoscope 1 are known and thus detailed description of such components will be omitted.

Next, a configuration of the bending portion 12 according to the present embodiment, which is to be provided in the insertion portion 2 of the endoscope 1, will be described below in detail with reference to FIGS. 3 and 4.

Inside the bending portion 12 according to the present embodiment, as illustrated in FIGS. 3 and 4, a bending tube for an endoscope (hereinafter simply abbreviated as "bending tube") 40 with a braid 28, which is a net-like tube, disposed so as to cover an outer periphery of a cylindrical body formed by pivotally joining the aforementioned distalmost end bending piece 23, the plurality of bending pieces 24 (24a, 24b) and the proximalmost end bending piece 25 via pivotal support portions 41 such as rivets is provided.

The braid 28 of the bending tube 40 is, for example, a tubular net-like body formed by fibers of a metal material such as a stainless steel material or a resin material such as aramid fiber are braided into a net-like shape.

Furthermore, the aforementioned bending rubber 26 is provided so as to cover an outer periphery of the braid 28. The bending rubber 26 is formed by, e.g., a thermal plastic elastomer having good heat and abrasion resistance and good thermal weldability.

Four operation wires 29 are inserted inside the bending tube 40. Each of the operation wires 29 is inserted inside a coil tube 29a from the flexible tube portion 13 to the inside of the operation portion 3.

The four operation wires 29 are pulled/loosened in a longitudinal direction of the insertion portion 2 by means of an operation to pivot the upward/downward bending operation knob 4 and the leftward/rightward bending operation knob 5 of the operation portion 3, which are illustrated in FIG. 1. Consequently, the respective bending pieces 23, 24 (24a, 24b), 25 are pivoted via the respective pivotal support portions 41 and the bending tube 40 bends in a desired direction, whereby the entire bending portion 12 bends.

The braid 28 of the bending tube 40 provided here is disposed so as to cover only the outer periphery of the plurality of bending pieces 24 (24a, 24b) except the distalmost end bending piece 23 and the proximalmost end bending piece 25, and is intended to protect the plurality of bending pieces 24 (24a, 24b) in the bending tube 40.

A distal end of the braid 28 is brazed via a brazing material such as solder to an outer peripheral portion of a bending piece 24a, which is a first bending piece that is the second from the distal end side, connected to the distalmost end bending piece 23 via a pivotal support portion 41. Likewise, a proximal end of the braid 28 is brazed via a brazing material such as solder to an outer peripheral portion of a bending piece 24b, which is a second bending piece that is the second from the proximal end side, connected to the proximalmost end bending piece 25 via a pivotal support portion 41.

In other words, the opposite ends of the braid 28 are fixed via brazing to the respective outer peripheral portions of the bending pieces 24a, 24b that are the second from the opposite ends of the bending tube 40.

Note that, as illustrated in FIG. 5, a maximum diameter d2 of the bending piece 24a that is the second from the distal end side and is covered by the braid 28 is set to be small relative to a maximum diameter d1 of the distalmost end bending piece 23 not covered by the braid 28 (d1>d2).

Likewise, as illustrated in FIG. 6, a maximum diameter d4 of the bending piece 24b that is the second from the proximal end side and is covered by the braid 28 is set to be small relative to a maximum diameter d3 of the proximalmost end bending piece 25 not covered by the braid 28 (d3>d4).

Note that the maximum diameter d1 of the distalmost end bending piece 23 and the maximum diameter d3 of the proximalmost end bending piece 25 are set to be substantially equal to each other (d1≈d3). Furthermore, the maximum diameter d2 of the second bending piece 24a from the distal end side and the maximum diameter d4 of the second bending piece 24b from the proximal end side are set to be substantially equal to each other (d2≈d4).

Also, a maximum diameter of a plurality of bending pieces 24 provided so as to continuous with one another between the second bending piece 24a from the distal end side and the second bending piece 24b from the proximal end side is set to be substantially equal to the maximum diameters d2, d4 of the bending piece 24a and the bending piece 24b.

A differential value (d1−d2) between the maximum diameter d1 of the distalmost end bending piece 23 and the maximum diameter d2 of the second bending piece 24a from the distal end side is set to be no less than twice a thickness of the brazed braid 28. Likewise, a differential value (d3−d4) between the maximum diameter d3 of the proximalmost end bending piece 25 and the maximum diameter d4 of the second bending piece 24b from the proximal end side is set to be no less than twice the thickness of the brazed braid 28.

In other words, in the bending tube 40, a maximum diameter (d2+2w1) including a thickness w1 of the braid 28 covering the second bending piece 24a of the distal end side and the second bending piece 24b from the proximal end side, to which the braid 28 is fixed via brazing, is set to be substantially equal to the maximum diameter d1 of the distalmost end bending piece 23 and also to the maximum diameter d3 of the proximalmost end bending piece 25 (d1≈d3≈d2+2w1).

Likewise, in the bending tube 40, a maximum diameter (d4+2w2), including a thickness w2 of the braid 28, of the plurality of bending pieces 24 covered by the braid 28, which is provided to be continuous with one another between the bending piece 24a and the bending piece 24b, is set to be substantially equal to the maximum diameter d1 of the distalmost end bending piece 23 and also to the maximum diameter d3 of the proximalmost end bending piece 25 (d1≈d3≈d4+2w2).

Consequently, in a state in which the bending tube 40 is covered by the braid 28, an outer diameter of the bending tube 40 from the distalmost end bending piece 23 to the proximalmost end bending piece 25 is substantially uniform. Thus, the bending portion 12 can have a smooth outer shape with no irregularities in its entirety even in a state in which the bending tube 40 is covered by the bending rubber 26.

According to the above description, the endoscope 1 according to the present embodiment can have a smooth outer shape with no irregularities in its entirety as a result of elimination of irregularities at a joint part between the distal end portion 11 and the bending portion 12 and a joint part between the bending portion 12 and the flexible tube portion 13.

Consequently, in the endoscope 1, the insertion portion 10 from the bending portion 12 to the flexible tube portion 13 has a substantially uniform outer diameter that has no irregularities and agrees with an outer diameter of the distal end portion 11, enabling a diameter of the insertion portion 10 to be reduced as much as possible compared to the conventional configurations. Therefore, the endoscope 1 enables enhancement in insertability of the insertion portion 10 to be inserted into a subject/object.

Furthermore, as illustrated in FIG. 5, a clearance C1 formed between the distalmost end bending piece 23 and the second bending piece 24a from the distal end side is set to be smaller than a clearance C2 formed between the respective bending pieces 24 provided to be continuous with one another on the proximal end side from the bending piece 24a (C1<C2) where the bending tube 40 is in a linear state.

Then, the clearance C1 is set to be smaller than twice a thickness t1 of a part of the bending rubber 26, the part covering the distalmost end bending piece 23 and the second bending piece 24a from the distal end side (C1<2t1).

Likewise, as illustrated in FIG. 6, a clearance C3 formed between the proximalmost end bending piece 25 and the second bending piece 24b from the proximal end side is set to be smaller than the clearance C2 formed between the respective bending pieces 24 provided to be continuous with one another on the distal end side from the bending piece 24b (C3<C2) where the bending tube 40 is in a linear state.

Then, the clearance C3 is set to be smaller than twice a thickness t2 of a part of the bending rubber 26, the part covering the proximalmost end bending piece 25 and the second bending piece 24b from the proximal end side (C3<2t2).

Note that where the bending tube 40 is in a linear state, the clearance C1 and the clearance C3 are set to be substantially equal to each other (C1≈C3).

In other words, where the bending tube 40 here is in a linear state, the respective clearances C1, C3 formed between the distalmost end bending piece 23 and the second bending piece 24a from the distal end side and between the proximalmost end bending piece 25 and the second bending piece 24b from the proximal end side are set to be smaller than the clearance C2 formed between the respective bending pieces 24 provided so as to be continuous with one another between the bending pieces 24a, 24b (C1≈C3<C2). Note that in a relationship among the clearances C1 to C3, a dimension of the clearances C1, C3 is set to be, for example, no more than 80% of a dimension of the clearance C2.

Furthermore, here, the thickness t1 and the thickness t2 of the bending rubber 26 are set to be substantially equal to each other (t1≈t2).

In other words, the clearances C1, C3 are set to be smaller than twice the thicknesses t1, t2 of the respective parts of the bending rubber 26, the parts covering the distalmost end bending piece 23 and the second bending piece 24a from the distal end side, and the proximalmost end bending piece 25 and the second bending piece 24b from the proximal end side, respectively, (C1≈C3<2t1≈2t2) where the bending tube 40 is in a linear state.

Consequently, even if the bending portion 12 has a configuration in which only a part from the second bending piece 24a from the distal end side to the second bending piece 24b from the proximal end side is covered by the braid 28, the bending rubber 26 is not caught in the clearances C1, C3 not covered by the braid 28 and thus the bending rubber 26 is prevented from being cut and damaged.

According to the above description, the endoscope 1 according to the present embodiment can have a configuration in which an outer periphery of a part of the bending portion 12 from the second bending piece 24a from the distal end side to the second bending piece 24b from the proximal end side is covered by the braid 28, the bending rubber 26 covering the braid 28 is thus prevented from entering the clearances C2 formed between the plurality of bending pieces 24a, 24, 24b, the bending rubber 26 is prevented from being caught in the clearances C1, C3 not covered by the braid 28 and the bending rubber 26 is thus prevented from being cut and damaged.

MODIFICATION

A distal end portion 11 of an endoscope 1 may have a large diameter depending on a configuration of incorporated components, such as whether or not a treatment instrument channel 21 and a forward water feeding conduit are provided. Also, a distal end portion 11 of an endoscope 1 may also have a large diameter as a result of provision of an image pickup unit 30 that forms a high-quality image. Furthermore, a distal end portion 11 of an endoscope 1 may be long as a result of provision of any of various image pickup units 30 such as those for special light and those having a zoom function.

As described above, distal end portions 11 of endoscopes 1 have specifications that differ according to the models, and the distal end portions 11 have, e.g., different outer diameters and lengths so as to comply with the different specifications. Thus, in the distal end portions 11, respective distal end rigid members 20 have, e.g., different outer diameters and length according to the different specifications. For conventional endoscopes 1, respective dedicated bending portions 12 configured to match distal end portions 11 having different specifications are provided.

Also, in endoscopes 1, flexible tube portions 13 provided so as to be continuous with proximal ends of respective bending portions 12 have different outer diameters because such flexible tube portions 13 have different specifications, for example, some of such flexible tube portions 13 is provided with a hardness changing mechanism.

Therefore, in the present modification, as illustrated in FIG. 7, a bending tube unit 40a of a bending portion 12 that can be fitted in common to distal end portions 11a, 11b and flexible tube portions 13a, 13b having different specifications will be described.

More specifically, the bending tube unit 40a here includes a bending piece 24a that is the second from the distal end side, a plurality of bending pieces 24 and a bending piece 24b that is the second from the proximal end side, and a braid 28 covering a periphery of the bending pieces 24a, 24, 24b. The braid 28 here is also fixed to the opposite-ends bending pieces 24a, 24b via brazing.

In other words, in the bending tube unit 40a, the respective bending pieces 24a, 24, 24b are joined to one another via respective pivotal support portions 41. The braid 28 is disposed so as to cover the periphery of the joined bending pieces 24a, 24, 24b.

Next, in the bending tube unit 40a, a distal end part of the braid 28 is fixed to the bending piece 24a via brazing using a brazing material such as solder, and subsequently, a proximal end part of the braid 28 is fixed to the bending piece 24b via brazing using a brazing material such as solder. Note that fixing of the braid 28 to the bending piece 24a or the bending piece 24b may be performed in an order with the distal end and the proximal end reversed.

The bending tube unit 40a configured as above enables the bending piece 24a that is the second from the distal end side to be joined to distalmost end bending pieces 23a, 23b fixedly fitted in advance on distal end rigid members 20a, 20b provided in the distal end portions 11a, 11b having different specifications, via a pivotal support portion 41.

Note that the respective distal end rigid members 20a, 20b provided in the distal end portions 11a, 11b have different specifications such as outer diameters and lengths. Thus, the distalmost end bending pieces 23a, 23b fixedly fitted on the distal end rigid members 20a, 20b have respective different specifications such as outer diameters and fitting lengths.

Likewise, the bending tube unit 40a enables the bending piece 24b that is the second from the proximal end side to be joined to proximalmost end bending pieces 25a, 25b fixedly fitted in advance on connection pipe sleeves 27a, 27b provided in the flexible tube portions 13a, 13b having different specifications, via a pivotal support portion 41.

Note that the connection pipe sleeves 27a, 27b provided at respective distal ends of the flexible tube portions 13a, 13b having different specifications also have respective different specifications such as outer diameters and lengths. Thus, the proximalmost end bending pieces 25a, 25b fixedly fitted on the connection pipe sleeves 27a, 27b have respective different specifications such as outer diameters and fitting lengths.

As described above, use of a common bending tube unit 40a to be provided in a bending portion 12 of an insertion portion 10, for various endoscopes 1 including distal end portions 11a, 11b and flexible tube portions 13a, 13b having different specifications enables not only easy management of parts in manufacture but also cost reduction as a result of mass production due to the use of the common bending tube unit 40a.

Furthermore, use of a common bending tube unit 40a to be provided inside bending portions 12 enables enhancement in assemblability of insertion portions 10 of endoscopes 1.

Although not illustrated, operation wires 29 may be fixed in advance to the distalmost end bending pieces 23a, 23b. Also, the proximalmost end bending pieces 25a, 25b and connection pipe sleeves 27a, 27b in the flexible tube portions may be integrated to directly join the bending tubes and the flexible tube portions via respective pivotal support portions 41.

The respective configurations of the embodiment and each modification described above may be combined. In other words, the invention described in the above embodiment is not limited to the embodiment and the modification and various modifications are possible without departing from the spirit of the invention in the practical phase. Furthermore, the above-described embodiment includes various phases of the invention, and various aspects of the invention may be extracted by arbitrary combinations of the plurality of elements disclosed.

For example, even where some elements are deleted from all the elements indicated in the above embodiment, a configuration with such elements deleted may be extracted as an aspect of the invention if such configuration can solve the aforementioned problem and provide the aforementioned effect.

What is claimed is:

1. A bending tube for an endoscope, the bending tube being provided inside a bending portion of an insertion portion of an endoscope and including a plurality of bending pieces pivotally joined to one another and covered by a soft outer covering, the bending tube comprising:

among the plurality of bending pieces, a distalmost end bending piece connected to a distal end portion of the insertion portion;

among the plurality of bending pieces, a proximalmost end bending piece connected to a flexible tube portion of the insertion portion;

a first bending piece including a distal end part pivotally joined to the distalmost end bending piece, the first bending piece having an outer diameter smaller than an outer diameter of the distalmost end bending piece;

a second bending piece including a proximal end part pivotally joined to the proximalmost end bending piece, the second bending piece having an outer diameter smaller than an outer diameter of the proximalmost end bending piece; and a net-like tube covering the plurality of bending pieces except the distalmost end bending piece and the proximalmost end bending piece, the net-like tube including a distal end part and a proximal end part fixed to an outer peripheral face of the first bending piece and an outer peripheral face of the second bending piece, respectively.

2. The bending tube for an endoscope according to claim 1, wherein in a state in which the plurality of bending pieces are arranged linearly, a clearance formed between the distalmost end bending piece and the first bending piece is smaller than a clearance formed between other bending pieces of the plurality of bending pieces.

3. The bending tube for an endoscope according to claim 2, wherein the clearance formed between the distalmost end bending piece and the first bending piece is smaller than twice a thickness of the outer covering.

4. The bending tube for an endoscope according to claim 1, wherein in a state in which the plurality of bending pieces are arranged linearly, a clearance formed between the proximalmost end bending piece and the second bending piece is smaller than a clearance formed between other bending pieces of the plurality of bending pieces.

5. The bending tube for an endoscope according to claim 4, wherein the clearance formed between the proximalmost end bending piece and the second bending piece is smaller than twice a thickness of the outer covering.

6. The bending tube for an endoscope according to claim 1, wherein use of a pivoting shaft usable in common for plural types of the distalmost end bending pieces having different specifications enables the plural types of the distalmost end bending pieces to be selectively joined to the first bending piece.

7. The bending tube for an endoscope according to claim 1, wherein use of a pivoting shaft usable in common for plural types of the proximalmost end bending pieces having different specifications enables the plural types of proximalmost end bending pieces to be selectively joined to the second bending piece.

8. An endoscope comprising the bending tube for an endoscope according to claim 1.

9. A method for manufacturing a bending tube for an endoscope, the bending tube being provided inside a bending portion of an insertion portion in an endoscope and including a plurality of bending pieces pivotally joined to one another and covered by a soft outer covering, the method comprising:

pivotally joining a plurality of small-diameter bending pieces except a distalmost end bending piece connected to a distal end portion of the insertion portion and a proximalmost end bending piece connected to a flexible tube portion of the insertion portion from among the plurality of bending pieces, the plurality of small-diameter bending pieces having an outer diameter smaller than an outer diameter of the distalmost end bending piece and an outer diameter of the proximalmost end bending piece;

covering an outer periphery of the plurality of small-diameter bending pieces joined, by a net-like tube; and fixing opposite ends of the net-like tube to opposite ends of the plurality of small-diameter bending pieces joined, respectively.

10. The method for manufacturing a bending tube for an endoscope according to claim 9, further comprising pivotally joining the opposite ends of the plurality of small-diameter bending pieces to the distalmost end bending piece and the proximalmost end bending piece, respectively.

* * * * *